US00PP29077P3

(12) United States Plant Patent
Urwin

(10) Patent No.: US PP29,077 P3
(45) Date of Patent: Mar. 6, 2018

(54) LAVENDER PLANT NAMED 'RIVERINA MARGARET'

(50) Latin Name: ***Lavandula* hybrid**
Varietal Denomination: Riverina Margaret

(71) Applicant: Nigel Alexander Russell Urwin, Lake Cathie (AU)

(72) Inventor: Nigel Alexander Russell Urwin, Lake Cathie (AU)

( * ) Notice: Subject to any disclaimer, the term of this patent is extended or adjusted under 35 U.S.C. 154(b) by 0 days.

(21) Appl. No.: 15/330,171

(22) Filed: Aug. 18, 2016

(65) Prior Publication Data

US 2017/0064898 P1 Mar. 2, 2017

(30) Foreign Application Priority Data

Aug. 26, 2015 (NZ) ..... PBR 32847

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Susan McCormick Ewoldt

(57) ABSTRACT

A new cultivar of Lavender plant named 'Riverina Margaret' that is characterized by purple flowers with light pink sterile bracts and green foliage.

1 Drawing Sheet

Botanical classification: *Lavandula* hybrid.
Variety denomination: 'Riverina Margaret'.

BACKGROUND OF THE INVENTION

The present invention relates to a new and distinct cultivar of Lavender plant botanically known as *Lavandula* hybrid and hereinafter referred to by the cultivar name 'Riverina Margaret'.

In 2004, approximately 90 Lavender plants were removed from an outdoor bed in a cultivated area of Wagga Wagga, New South Wales Australia. The outdoor bed contained many different hybrid Lavender plants. The 90 Lavender plants were grown in containers and observed in Wagga Wagga, New South Wales, Australia. 'Riverina Margaret' was discovered in 2005 as a single plant from among the 90 Lavender plants based on flower color and overall plant shape. The exact parent plants are unknown.

Asexual reproduction of the new cultivar 'Riverina Margaret' by terminal cuttings was first performed in 2005 in Wagga Wagga, New South Wales, Australia. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Lavender cultivar 'Riverina Margaret'. These traits in combination distinguish 'Riverina Margaret' as a new and distinct cultivar.

1. Lavender 'Riverina Margaret' exhibits purple flowers with light pink sterile bracts.
2. Lavender 'Riverina Margaret' exhibits green foliage.

The closest comparison cultivar is Lavender 'Tinkled Pink' (not patented). 'Riverina Margaret' is different than 'Tinkled Pink' in having lighter pink sterile bracts and a more spreading habit. In comparison, 'Tinkled Pink' has a more upright habit and darker pink sterile bracts.

BRIEF DESCRIPTION OF THE DRAWING

The accompanying photograph illustrates the distinguishing traits of Lavender 'Riverina Margaret'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Lavender cultivar named 'Riverina Margaret'. Data was collected in Auckland, New Zealand from 9 month old outdoor grown plants. The time of year was summer in the Southern Hemisphere and the average temperature was 20 to 26° Centigrade during the day and 12 to 18° Centigrade at night. Color determinations are in accordance with The Royal Horticultural Society Colour Chart 2015 edition, except where general color terms of ordinary dictionary significance are used. The growing requirements are similar to the species. 'Riverina Margaret' has not been tested under all possible conditions and phenotypic differences may be observed with variations in environmental, climatic, and cultural conditions, however, without any variance in genotype.

Botanical classification: *Lavandula* hybrid 'Riverina Margaret'.
Use: Ornamental Perennial.
Parentage: The exact parent plants of 'Riverina Margaret' are unknown.
Vigor: Moderate.
Container size: 10 cm. and larger.
Growth habit: Upright, outwardly spreading.
Plant shape: Rounded with erect flower spikes.

Height: Average 20 cm. in height.
Width: Average 20 cm. in width.
Hardiness: −9° to 38° C.
Propagation: Terminal cuttings.
Crop time: 9 months.
Stem:
*Branching habit*.—Free branching.
*Number of lateral branches*.—Approximately 4.
*Lateral branch dimensions*.—2 mm. in width and 8.0 cm. in length.
*Lateral branch strength*.—Strong.
*Color*.—N148A.
*Pubescence*.—Lightly covered with short hairs.
*Internode length*.—2.5 mm. between nodes.
*Shape*.—Square in cross-section.
Foliage:
*Leaf arrangement*.—Opposite.
*Compound or single*.—Single.
*Quantity of leaves per lateral branch*.—10.
*Leaf shape*.—Linear.
*Leaf apex*.—Acute.
*Leaf base*.—Cuneate.
*Leaf length*.—2.0 to 3.5 cm. in length.
*Leaf width*.—2.75 to 5.3 cm. in width.
*Texture* (*both sides*).—Velvety.
*Pubescence*.—Soft short hairs on upper side, absent on bottom side.
*Leaf margin*.—Entire.
*Vein pattern*.—Linear midrib with anastomoses veinlets.
*Young leaf color* (*upper surface*).—147A.
*Young leaf color* (*lower surface*).—147B.
*Mature leaf color* (*upper surface*).—147B.
*Mature leaf color* (*lower surface*).—147B.
*Vein color* (*both surfaces*).—147B.
*Leaf attachment*.—Sessile.
*Leaf fragrance*.—Aromatic, pungent.
Flower:
*Flower arrangement*.—Terminal cylindrical spikes.
*Inflorescence dimensions*.—3.5 to 4.0 cm. in length and 1.2 to 1.5 cm. in diameter.
*Quantity of flowers and buds per inflorescence*.—Approximately 35.
*Flowering season*.—Spring to Summer.
*Time to flower or response time*.—4 to 6 weeks after buds form.
*Fragrance*.—Musk scent.
*Self-cleaning or persistent*.—Self cleaning.
*Flower bud length*.—2.0 mm. in length.
*Flower bud diameter*.—0.75 mm. in diameter.
*Flower bud shape*.—Ovate.
*Bud color*.—N92D.
*Flower aspect*.—Outward.
*Flower shape*.—Salverform.
*Flower dimensions*.—2 mm. in diameter and 5.5 mm. in height.
*Flower longevity*.—Lasts approximately 20 days.
*Petal arrangement*.—Rotate with five petals fused into a tube.
*Petal shape*.—Spathulate.
*Petal margin*.—Entire.
*Petal apex*.—Rounded.
*Petal texture* (*both surfaces*).—Hirsute.
*Petal dimensions*.—5 mm. in length and 0.7 mm. in width.
*Petal color when opening* (*upper side*).—N92C.
*Petal color when opening* (*under side*).—N92C.
*Petal color when fully opened* (*upper side*).—N92C.
*Petal color when fully opened* (*under side*).—N92C.
Sepals:
*Sepal number*.—5.
*Sepal shape*.—Linear.
*Sepal apex*.—Acute.
*Sepal base*.—Fused.
*Sepal margin*.—Entire.
*Sepal texture* (*both surfaces*).—Covered with soft hairs.
*Sepal dimensions*.—5.3 mm. in length and 1.7 mm. in width.
*Sepal color* (*both surfaces*).—147C.
Calyx:
*Calyx shape*.—Tubular.
*Calyx dimensions*.—5.3 mm. in length and 1.7 mm. in diameter.
Peduncle:
*Peduncle dimensions*.—14 mm. in length and 1.5 mm. in diameter.
*Peduncle color*.—N148A.
*Peduncle strength*.—Medium.
Sterile bracts:
*Sterile bract location*.—On top of each spike.
*Sterile bract quantity*.—4.
*Sterile bract shape*.—Oblanceolate.
*Sterile bract apex*.—Rounded.
*Sterile bract base*.—Cuneate.
*Sterile bract margin*.—Entire, undulating.
*Sterile bract texture* (*both surfaces*).—Velvety.
*Sterile bract dimensions*.—20.0 mm. in length and 7.0 mm. in width.
*Sterile bract color* (*upper side*).—N78C.
*Sterile bract color* (*under side*).—N78C.
Reproduction organs:
*Stamen number*.—4.
*Anther shape*.—Oval.
*Anther length*.—0.5 mm. in length.
*Anther color*.—N92C.
*Amount of pollen*.—Moderate.
*Pollen color*.—2C.
*Pistil number*.—1 in number.
*Pistil length*.—3.0 mm.
*Stigma shape*.—Claviform.
*Stigma color*.—N92D.
*Style length*.—2.0 mm.
*Style color*.—155C.
*Ovary color*.—137C.
Fruit and seed production: Plants of the new Lavender have not been observed for fruit and seed production.
Disease and pest resistance: Plants of the new Lavender have not been observed for disease or pest resistance.

The invention claimed is:

1. A new and distinct variety of Lavender plant named 'Riverina Margaret' as described and illustrated.

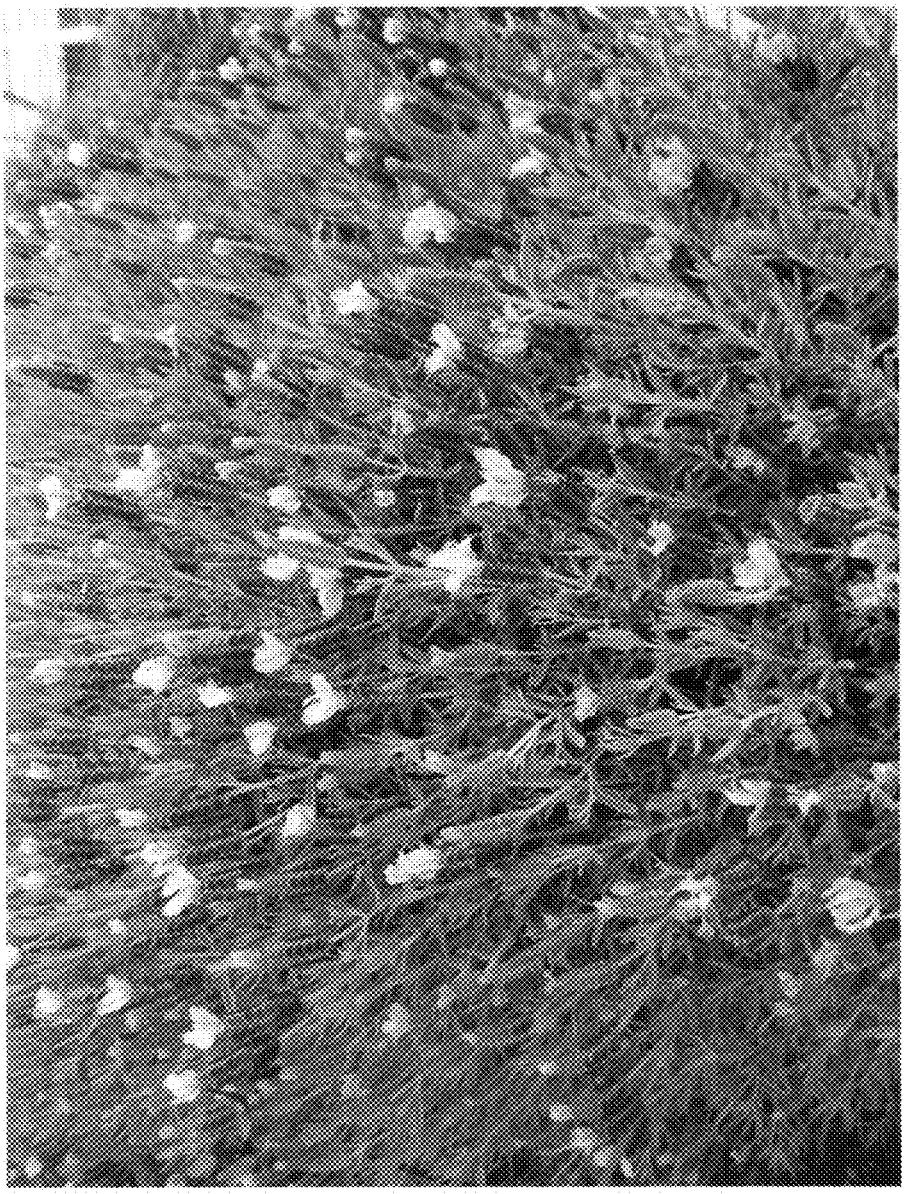

* * * * *